United States Patent [19]

Khera

[11] 4,077,907

[45] Mar. 7, 1978

[54] CATALYST FOR SYNTHESIZING LOW BOILING ALIPHATIC HYDROCARBONS FROM CARBON MONOXIDE AND HYDROGEN

[75] Inventor: Surjit Singh Khera, Upper Arlington, Ohio

[73] Assignee: Battelle Development Corporation, Columbus, Ohio

[21] Appl. No.: 796,890

[22] Filed: May 16, 1977

Related U.S. Application Data

[62] Division of Ser. No. 635,845, Nov. 28, 1975.

[51] Int. Cl.$^2$ .................... B01J 21/04; B01J 23/80; B01J 27/04
[52] U.S. Cl. ................................. 252/439; 252/466 J
[58] Field of Search ............................ 252/439, 466 J

[56] References Cited

U.S. PATENT DOCUMENTS

| | | | |
|---|---|---|---|
| 2,211,022 | 8/1940 | Michael et al. | 260/449.6 |
| 2,231,990 | 2/1941 | Dreyfus | 260/449.6 |
| 3,962,138 | 6/1976 | Ray et al. | 252/466 J |
| 3,988,263 | 10/1976 | Hansford | 252/466 J |

*Primary Examiner*—W. J. Shine

*Attorney, Agent, or Firm*—Kenneth R. Warburton

[57] ABSTRACT

Low boiling ($C_1$ to $C_4$) aliphatic hydrocarbons are obtained by passing a mixture of hydrogen and carbon monoxide at a molar ratio of about 1:2 to 2:1 at a temperature between about 350° and about 450° C. and a pressure of about 600 p.s.i.g. to about 10,000 p.s.i.g. at a volumetric hourly space velocity of about 200 to about 6000 in contact with catalyst comprising a sulfided, interspersed mixture of cobalt oxide, aluminum oxide and zinc oxide. The catalyst, prior to sulfiding, comprises about 1 to about 15 weight percent of cobalt oxide, about 55 to about 85 weight percent of aluminum oxide and about 15 to about 30 weight percent of zinc oxide. In preparing the catalyst, the cobalt, aluminum and zinc can be separately precipitated as the corresponding hydroxides and then admixed prior to calcination, or two or more of such metals can be coprecipitated as the hydroxides at a controlled pH with ammonium hydroxide from the corresponding aqueous nitrate solutions and then admixed with each other. The admixed hydroxides of cobalt, aluminum and zinc are then dried, calcined and sulfided. The sulfur content of the catalyst by elemental analysis, comprises about 2.0 to 12.0 percent by weight of the final catalyst composition.

4 Claims, No Drawings

CATALYST FOR SYNTHESIZING LOW BOILING ALIPHATIC HYDROCARBONS FROM CARBON MONOXIDE AND HYDROGEN

This is a division of application Ser. No. 635,845, filed Nov. 28, 1975.

This invention relates to a process for catalytically synthesizing low boiling ($C_1$ to $C_4$) aliphatic hydrocarbons from mixtures of carbon monoxide with hydrogen and to a catalyst for use in the synthesis of the low boiling aliphatic hydrocarbons.

BACKGROUND OF THE INVENTION

It is well known that there is an increasing shortage of natural gas (chiefly methane) in the United States and there is a generally limited supply of natural gas throughout the world. For this reason, attention is being directed to a substitute or supplement for natural gas. It is also well known that there is an increasing demand for other low boiling hydrocarbons for use as fuels themselves, for gas enrichment and for use in synthesizing certain organic compounds.

The synthesis of low boiling aliphatic hydrocarbons by hydrogenating carbon monoxide is not a new concept. In fact, the synthesis of methane by hydrogenating carbon monoxide was first described by P. Sabatier and J. B. Senderens in 1902 (Compt. Rend. 134, 514 and 689 [1902]). Higher boiling hydrocarbons were obtained from carbon monoxide and hydrogen in the early 1920's by F. Fischer and H. Tropsch (Chem. Ber. 56, 2428 [1923]). While, at the present time, processes are available for producing a full range of hydrocarbons by hydrogenating carbon monoxide, the economics of such processes has mitigated against their wide-spread commercialization. The products obtained in the catalytic hydrogenation of carbon monoxide can be one or more materials selected from hydrocarbons, alcohols, aldehydes, ketones, esters, ethers and fatty acids of almost any chain length, degree of saturation and structure. The relative extent to which one or more of these products is obtained can be controlled to some extent by the selection of the catalyst composition and operating conditions. Catalysts which heretofore have been of special interest in the synthesis of organic compounds from carbon monoxide and hydrogen are those wherein the metal component is selected from iron, cobalt, nickel, ruthenium, zinc and thorium. The behavior of these catalysts in hydrogenating carbon monoxide is dependent to a large extent upon the presence of chemical and structural promotors, upon the method used in preparing the catalyst, upon the catalyst surface conditions, upon the reaction conditions and upon the nature or make-up of the feed gas mixture, i.e., synthesis gas charged to the reaction system.

Nickel has been used as a catalyst for the synthesis of methane according to the reaction

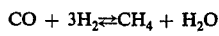  (1)

which proceeds from left to right at temperatures below about 500° C. and in the opposite direction at higher temperatures.

Cobalt admixed with thorium dioxide and magnesium oxide, as promotors, and kieselguhr, as a carrier, has been used as a catalyst for the synthesis of higher aliphatic hydrocarbons. (F. Fischer and H. Tropsch, Brennstoff-Chem. 7, 97 [1926]; and F. Fischer and H. Pichler, Brennstoff-Chem 20, 41, 221 and 247 [1939]).

Iron has been used as a catalyst for the synthesis of aliphatic and aromatic hydrocarbons. In the past, alkali has been used as a promotor when the catalyst contains iron. The alkali is reported to influence surface conditions of the catalyst and to enhance the production of higher molecular weight products. In the early work conducted by F. Fischer and H. Tropsch, alkali-promoted iron-copper catalysts were employed in producing high boiling (gasoline range) hydrocarbons. (F. Fischer and H. Tropsch, Brennstoff-Chem. 9, 21 [1928]. The promoting effect of alkali to iron catalysts was believed to be the result of the formation in its presence of ferric oxide ($Fe_2O_3$) and the prevention of its transition to the less active magnetic iron oxide ($Fe_3O_4$). (G. LeClerc, Compt. Rend 207, 1099 [1939]).

In accordance with the present invention the presence of alkali in the catalyst is kept at a minimum since it is believed that the presence of alkali in the catalyst of the invention causes the catalyst to fuse and thus materially decrease the surface available for catalytic purposes.

Sintered iron catalysts have previously been used in preparing branched-chain paraffins. These catalysts have been prepared by reducing precipitated iron-alumina catalysts at 1550° F. (British Pat. No. 473,932 [1937]; British Pat. No. 474,448 [1937]; and British Pat. No. 496,880 [1938]).

Ruthenium and ruthenium-containing catalysts have been used in the synthesis of high-melting waxes from hydrogen and carbon monoxide (H. Pichler, Brennstoff-Chem. 19, 226 [1938]; H. Pichler and H. Buffleb, Brennstoff-Chem. 21, 257, 273 and 285 [1940]). Other Group VIII metals, i.e., rhodium, palladium, osmium, iridium and platinum have been less satisfactory than ruthenium (U.S. Pat. No. 1,628,190 [1927]). The effect of pressure upon the yield and type of products with ruthenium catalysts is very pronounced.

Zinc oxide and mixtures of zinc oxide with chromic oxide have been used as catalysts for synthesizing methanol from hydrogen and carbon monoxide at temperatures above 300° C. and pressures above 200 atmospheres. (H. Pichler, Brennstoff—Chem. 33, 289 [1952]).

Oxide catalysts, in general, show a smaller degree of activity toward carbon monoxide plus hydrogen than the metal catalysts. On the other hand, metal catalysts, e.g., nickel, cobalt, iron and ruthenium, are more sensitive to sulfur and sulfur compounds than oxide catalysts.

Prior processes for hydrogenating carbon monoxide to methane and other low boiling hydrocarbons have required hydrogen to carbon monoxide ratios in the order of about 3:1 (see equation 1 hereinabove). Therefore, in many instances, it has been necessary to increase the hydrogen content of synthesis gas by the so-called water gas shift reaction, i.e.,

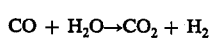  (2)

The carbon dioxide formed in the water gas shift reaction is then removed by compressing the gas and scrubbing it with water or by reacting it with ethanolamines. The hydrogen thus obtained is used to increase the hydrogen to carbon monoxide ratio in synthesis gas to an amount of about 2:1 to 3:1, preferably the latter, i.e., about 3:1.

Coal has been used in the production of synthetic or substitute natural gas (SNG) comprising low boiling hydrocarbons according to the Lurgi process as described by Paul F. H. Rudolph in Chemical Age of India, 25, 289–299 (1974). In the Lurgi process for producing SNG from coal, five separate steps are required: (1) pressure gasification of coal to recover gaseous products and remove ash and tar; (2) crude gas shift conversion wherein steam is reacted with some carbon monoxide to form carbon dioxide and hydrogen, the latter being used to increase the hydrogen to carbon monoxide ratio in the synthesis gas; (3) Rectisol gas purification wherein organic solvents remove impurities from the gas; (4) methane synthesis where the carbon monoxide and hydroden are reacted to produce methane; and (5) a Phenolsolvan process for treating the gas liquor from coal gasification to remove water-soluble components, e.g., phemols, ammonia and fatty acids.

In accordance with the present invention, a catalyst is provided for the hydrogenation of carbon monoxide to low boiling hydrocarbons wherein the $H_2$:CO ratio can be 1:1. Since this ratio is frequently obtained when coal is subjected to complete gasification, there is no need in the process of the present invention to employ a water gas shift reaction such as that used in the Lurgi process. While coal is an economic source of synthesis gas for use as feed gas in the process of the present invention, the synthesis gas can be obtained from any carbonaceous material which can be decomposed to hydrogen and carbon monoxide. Examples of such materials are fossil fuels such as natural gas, bituminous coal, lignite, oil shale, crude oil and residual fuel oils. For the most part, synthesis gas has been obtained from natural gas or coal. The theoretical ideal synthesis gas reaction may be represented as follows:

$$C + H_2O \rightarrow CO + H_2 \qquad (3)$$

One of the impurities frequently present in synthesis gas is sulfur or compounds of sulfur. As indicated hereinabove, metal catalysts such as nickel, cobalt, iron and ruthenium are poisoned by sulfur and sulfur compounds. Thus, synthesis gas containing sulfur or sulfur compounds has previously been subjected to a desulfurization process prior to being converted into hydrocarbons. One such process is the Girbitol process as described by C. B. Ames, Mines Magazine 32, 508 (1942). Other desulfurization processes include (1) the iron oxide process (C. C. Hall and A. R. Powell, Office of Technical Services Report No. PB288, Department of Commerce, Washington, D.C.); (2) the "Alkazid Process" (Lorenzen, Gerhard and Leithe, Gas and Wasserfach 86, 313 [1943]) in which an alkaline organic compound absorbs hydrogen sulfide and then is steam-stripped for reuse (H. A. Schade, E. Foran and R. C. Aldrich, Office of Technical Services Report No. PB373, Department of Commerce, Washington, D.C.); and (3) F. Fischer and H. Tropsch desulfurization by catalytic reduction of sulfur compounds to hydrogen sulfide (British Pat. No. 254,288 [1925]; British Pat. No. 282,634 [1926]; Canadian Pat. No. 266,382 [1926]; and German Pat. No. 558,558 [1926]).

A process for decomposing organic sulfur compounds to hydrogen sulfide by passing the gas at a temperature above 300° C. over a mixture of alkali metal carbonates and iron oxide is disclosed by Studien und Verwertungs G. m. b. H. in British Pat. No. 469,933 (1937) and German Pat. No. 651,462 (1937). In still another process I. G. Farbenindustrie A. G. has disclosed a process for decomposing organic sulfur compounds to hydrogen sulfide simultaneously with the water gas shift reaction (U.S. Pat. No. 1,695,130 [1928]).

SUMMARY OF THE INVENTION

In accordance with the present invention a catalyst is provided which is resistant to poisoning by sulfur or compounds of sulfur present in products of coal gasification. Thus, the present invention does not require the desulfurization of the synthesis gas prior to being catalytically converted to low boiling hydrocarbons.

The products with which the present invention is concerned are the $C_1$ to $C_4$ aliphatic hydrocarbons. The $C_1$ to $C_4$ aliphatic hydrocarbons are desirable fuel gases per se or they may be used for gas enrichment. They may also be used as intermediates in forming other organic compounds. Methane is widely used to upgrade manufactured gas. Ethane can be used in the production of ethylene. It is also useful in the production of acetic acid, acetaldehyde, ethyl chloride and nitroethane. Propane is widely used as a fuel in liquified petroleum gas (LPG). It is also used as a refrigerant in chemical, petroleum refining and gas processing operations. Still further, it is useful as a solvent and for injection into subterranean formations to increase the production of crude oils from oil wells.

Essentially, the present invention comprises a process for synthesizing low boiling aliphatic hydrocarbons from carbon monoxide and hydrogen. The process utilizes a novel catalyst comprising a sulfided, interspersed mixture of cobalt oxide, aluminum oxide and zinc oxide. According to the process, a synthesis gas comprising a mixture of hydrogen and carbon monoxide having a molar ratio of about 1:2 to 2:1, preferably 1:1, is passed through a reaction zone at a temperature of about 350° to about 450° C. and a pressure of about 600 p.s.i.g. to about 10,000 p.s.i.g. or higher, e.g. 25,000 p.s.i.g., at a space velocity (volume of gas per hour per volume of catalyst) of about 200 to about 6000 in contact with a catalyst comprising a sulfided, interspersed mixture of cobalt oxide, aluminum oxide and zinc oxide. A gaseous mixture comprising a mixture of low boiling aliphatic hydrocarbons is recovered from the reaction product. The preferred temperature range is about 375° to about 425° C.; the preferred pressure range is about 1000 to about 1500; and the preferred space velocity is about 900 to about 2300. Optimum values of temperature and pressure may vary according to the composition of the feed gas, type and amount of catalyst, throughput velocity and the like.

DETAILED DESCRIPTION OF THE INVENTION

The feed gas (synthesis gas) employed in the process of the invention may be obtained from a variety of carbonaceous materials. From an economic standpoint, it is preferred to use a low cost material such as bituminous coal, lignite, oil shale and low grade crude and residual fuel oils. Since sulfur is undesirable in pipeline gas, it is preferred to use a synthesis gas source material which contains little or no sulfur when preparing a pipeline gas. While sulfur can be removed from the pipeline gas prior to distribution, the purification step adds to the overall cost and may offset the advantage of using a low cost material in the first instance. The removal of sulfur, however, is not necessary insofar as the catalyst is concerned since the catalyst is not poisoned by sulfur. The synthesis gas is advantageously obtained by gasification of a low cost coal with steam. As indicated above, however, the process of the invention is not limited to the use of synthesis gas derived from coal but is applicable to mixtures of hydrogen and carbon monoxide, with or without other gaseous ingredients from any source. The presence of carbon dioxide in the synthesis gas has no deleterious affect on methanation. For methanation, the synthesis gas should contain hydrogen and carbon monoxide in a molar ratio of 1:2 to 2:1, preferably 1:1 since the primary reaction is $$2CO + 2H_2 \rightarrow CH_4 + CO_2 \quad (4)$$

The catalyst of the present invention comprises a sulfided, interspersed mixture of cobalt oxide, aluminum oxide and zinc oxide, which mixture by elemental analysis contains an alkali metal content of less than about 0.5 weight percent (preferably less than 0.1 weight percent). While care is taken to avoid the use of alkali metals in forming the oxides of cobalt, aluminum and zinc, a small amount, usually less than about 0.1 percent, of alkali metal, generally in the form of its oxide or sulfide, may appear in the catalyst as a result of impurities in some of the starting materials. The final catalyst composition, by elemental analysis, contains about 2.0 to about 12.0 weight percent of sulfur which has been incorporated into the catalyst by conventional sulfiding techniques. The proportion of cobalt oxide in the catalyst comprises about 1 to about 15 weight percent of the catalyst, preferably about 2 to about 10 weight percent. The proportion of aluminum oxide in the catalyst comprises about 55 to about 85 weight percent of the catalyst, preferably about 70 to about 80 weight percent. The proportion of zinc oxide in the catalyst comprises about 15 to about 30 weight percent of the catalyst, preferably about 20 to about 25 weight percent.

Even though each of the constituents in the catalyst of the present invention has been used in prior catalysts for hydrogenating carbon monoxide, I know of no catalyst consisting of a combination consisting of sulfided, interspersed mixture of cobalt oxide, aluminum oxide, and zinc oxide.

The catalyst of the invention can be prepared by any of several methods so long as by elemental analysis it contains alkali metal of less than 0.5 weight percent. The oxides of cobalt, aluminum and zinc can be separately prepared and then admixed with each other or any two or all three of such metal oxides can be formed in the presence of each other. Thus, the catalyst can be prepared by precipitating the metals from aqueous solutions thereof with a non-alkali metal electrolyte, then calcined and admixed or the precipitates can be admixed and then calcined. More specifically, the catalyst can be prepared by separately precipitating the hydroxides of cobalt, aluminum and zinc with ammonium hydroxide from the corresponding nitrates or acetates of such metals. The hydroxides can then be admixed, dried and calcined to form an interspersed mixture of the oxides of cobalt, aluminum and zinc. Alternatively, the hydroxides can be dried, then admixed and calcined. A further modification comprises drying the hydroxides, followed by calcining and then admixing the calcined products. In a preferred embodiment of the invention, cobalt and aluminum hydroxides are coprecipitated with ammonium hydroxide from an aqueous solution of the corresponding mixture of cobalt and aluminum nitrates. Coprecipitation is effected at a pH of from about 6.5 to about 6.9. Zinc hydroxide is separately precipitated from an aqueous solution of zinc nitrate at a pH of from about 6.3 to about 6.9. The hydroxides are then admixed, dried and calcined. After calcination, the mixture of oxides is sulfided to form a sulfided, interspersed mixture of the oxides of cobalt, aluminum and zinc.

Catalyst preparation is conducted under controlled conditions: generally a temperature of about room temperature (20° to 25° C.) to about 80° C.; a maintaining of the pH of the solution at a value within the range of from about 6.5 to about 6.9 for coprecipitating; and a maintaining of the pH of the solution at a value requisite for precipitation, generally of from about 9 to about 9.5, for precipitating separately the cobalt oxide and/or hydroxide. If the pH is not maintained as just taught, the resulting catalyst is less effective in the formation of low boiling hydrocarbons. To achieve this pH control, it may be necessary to add ammonia or similar substance, but not alkali, into the solution (suspension). Alkali is undesirable since an alkali content in the catalyst causes fusion of the catalyst. In that catalyst fusion will shorten catalyst operating life, for increased life and a practical operating life for the catalyst one preferably holds the alkali metal content by elemental analysis of the catalyst, to less than 0.1 weight percent. The pH is kept at a constant value, preferably through control by a pH meter. In a preferred embodiment of the invention, zinc is separately precipitated as the hydroxide, preferably with ammonium hydroxide, under controlled temperature conditions of about 60° to about 70° C., while maintaining the pH of the solution at a value within the range of from about 6.3 to about 6.9. The zinc hydroxide is then admixed with the cobalt and aluminum hydroxides prepared by a coprecipitation technique. The mixed hydroxides are then dried and/or calcined generally in the presence of oxygen or air. Drying may be effected under relatively mild conditions, for example, 8 to 16 hours at 100° to 120° C. Drying can amount to calcination so long as precipitated hydroxides convert to their oxides and the dried mixture is friable. Alternatively to such drying and calcination concurrently, one may calcinate, after drying, at higher temperatures, for example, at 300° to 400° C. for 2 to 10 hours to obtain a calcined catalyst in the form of mixed oxides.

The calcined catalyst, in which the mixed oxides are interspersed, can optionally be subjected to a reduction step. Reduction can be effected by heating the catalyst composition in the presence of hydrogen at an elevated temperature, normally at a temperature of about 300° to about 400° C. The hydrogen treatment or preactivation may change the oxidation state of the metals present or it may reduce at least a portion of the oxides to their metallic state. Depending upon the degree of reduction, the calcined catalyst may be treated with hydrogen at a temperature of about 300° to about 450° C. for a period of 5 minutes to 48 hours. Thereafter, the catalyst is treated with a sulfur compound, such as, for example, hydrogen sulfide in the vaporous or liquid phase in the presence of hydrogen to form a sulfided, interspersed mixture of cobalt, aluminum and zinc oxides.

Dried and/or calcined catalyst, and also that optionally hydrogen treated, for sulfiding is an interspersed mixture of cobalt, aluminum and zinc oxides. For teaching of the invention, the oxide of cobalt in this interspersed mixture also is referred to as "cobalt oxide". By "cobalt oxide" there is intended to mean each of and any mixture thereof of cobaltous oxide (CoO), cobaltic oxide ($Co_2O_3$), and cobalto-cobaltic oxide ($Co_3O_4$) also sometimes called cobaltosic oxide, in that which to all that are present as the oxide of cobalt for sulfiding depends upon the specific drying, calcination, and hydrogen treatments and conditions to which the precipitated hydroxides are subjected prior to sulfiding. Sulfiding can be effected by conventional sulfiding techniques. By sulfiding in the presence of hydrogen, any unsulfided cobalt oxide is believed to comprise cobaltous oxide and/or metallic cobalt. A preferred method comprises treating the catalyst with a hydrogen and hydrogen sulfide mixture at an elevated temperature in the range of about 300° to about 400° C., with the concentration of hydrogen in the vaporous mixture being at least 50 mol percent. The pressure in the treating zone will range from atmospheric to 1,000 p.s.i.g. for a period of about 0.1 to about 48 hours. Although not to be limited thereto, contact between the catalyst, hydrogen and hydrogen sulfide mixture can be effected by passing the gaseous mixture through a fixed bed of the catalyst. The sulfided catalyst composition normally contains about 2.0 to about 12.0 percent by weight of sulfur based on the final weight of the sulfided catalyst composition. In addition to hydrogen sulfide, other sulfiding agents such as low molecular weight mercaptans and organic sulfides can be employed in forming the sulfided catalyst. The catalyst may be formed into any desired shape such as, for example, granules, pills, pellets and the like.

It has been found that the use of a sulfided catalyst of the invention is particularly effective in the synthesis of low boiling aliphatic hydrocarbons from mixtures of hydrogen and carbon monoxide in the presence of sulfur compounds, such as hydrogen sulfide and mercaptans, since the sulfided catalyst of the invention is not poisoned by sulfur compounds. By contrast, conventional iron and nickel catalysts are rapidly poisoned by the presence of sulfur compounds necessitating extensive gas purification facilities to maintain catalyst activity. These facilities are not required when a sulfided catalyst of the invention is employed. Thus, the cost of producing fuel gas according to the process of the invention is substantially lower than the cost of producing fuel gas with conventional iron and nickel catalysts. In accordance with the present invention, coal may be gasified by reaction with steam at about 1,000 to 6,000 p.s.i.g. and at an elevated temperature of about 800° C. The product of such a reaction typically contains $H_2$, $CH_4$, $C_2H_6$, CO, $CO_2$ and some sulfur or sulfur-containing compounds. After removing the $CH_4$ and $C_2H_6$, the remaining gas can be subjected to the process of the present invention.

The process of the invention can be operated as a multistage or single stage process in either a fixed-bed or moving-bed reactor. Preferably, however, a recycle system, in which unconverted hydrogen and carbon monoxide are recycled to the reactor, is used. In any process according to the invention, temperature and pressure control in or between synthesis converters can be any suitable means such as, for example, feed gas preheaters, coolers, quenchers, compressors and the like.

The reaction of hydrogen with carbon monoxide in molar ratios of 1:2 to 2:1 and preferably about 1:1 to produce a low boiling ($C_1$ to $C_4$) aliphatic hydrocarbons is conducted at a temperature of about 350° to about 450° C., preferably about 375° to about 425° C., a space velocity (volume of gas per hour per volume of catalyst) of about 200 to about 6000, preferably about 900 to about 2300, and a pressure of about 600 to about 10,000 p.s.i.g., preferably about 1000 to about 1500 p.s.i.g., in the presence of a sulfided, interspersed mixture of cobalt oxide, aluminum oxide and zinc oxide having an alkali content of less than 0.5 percent alkali, based on the weight of the catalyst, and preferably less than 0.1 percent. The space velocity will depend to some extent upon the type of reaction system used. For fixed-bed reactors, the number of volumes of gas per volume of catalyst per hour, can be about 200 to about 6000 and is preferably about 900 to about 2300; for fluidized-bed operation using recycle, the total feel space velocity is much higher and may be about 3000 to about 5000.

The invention is further illustrated by reference to the following examples which are intended to be representative rather than restrictive of the scope of the invention.

EXAMPLE 1

Preparation of Catalyst

In this example, the hydroxides of cobalt, aluminum and zinc are precipitated separately and then admixed prior to drying according to the procedure which follows.

An aqueous solution of aluminum nitrate is prepared by dissolving 134.3 gms of aluminum nitrate in 1500 ml of distilled and deionized water. Ammonium hydroxide is added slowly to the aqueous solution of aluminum nitrate at room temperature until the pH of the solution is 6.2. Where room temperature is recited in this disclosure, including its examples, there is intended a temperature of between about 20° to 25° C, i.e. about 68° to 77° F. The pH is continuously measured while adding the ammonium hydroxide. The precipitate thus formed comprising aluminum hydroxide is separated from the reaction mass by filtration. It is then admixed in a beaker (A) with 500 ml of distilled and deionized water.

An aqueous solution of zinc acetate is prepared by dissolving 16.8 gms of zinc acetate in 1000 ml of distilled and deionized water. Ammonium hydroxide is added slowly to the aqueous solution of zinc acetate at room temperature until the pH of the solution is 6.8. The precipitate thus formed comprising zinc hydroxide is separated from the reaction mass by filtration and admixed with the aluminum hydroxide in beaker (A). The filtrate remaining after removal of the zinc hydroxide is then heated to about 70° C. to which is then added 10 ml of ammonium hydroxide. Additional zinc hydroxide which forms is separated from the reaction mass by filtration, washed with 200–500 ml of distilled water and admixed with the aluminum hydroxide and zinc hydroxide in beaker (A).

An aqueous solution of cobaltous nitrate is prepared by dissolving 2.46 gms of cobaltous nitrate in 400 ml of distilled and deionized water. Ammonium hydroxide is added slowly to the aqueous solution of cobaltous nitrate at 70° C. until the pH of the solution is 9.5. The precipitate thus formed comprising cobaltous hydroxide is separated from the reaction mass by filtration, washed with 400 ml of distilled water and admixed with the aluminum hydroxide and zinc hydroxide in beaker (A).

The mixture of cobaltous hydroxide, aluminum hydroxide and zinc hydroxide in beaker (A) is stirred at 70° C. for 2 hours. The beaker (A) containing the mixed hydroxides is then placed in an oven at 120° C. for 16 hours or more until the mixture is dry. A dark colored (almost black) hard aggregate is obtained. The aggregate is ground to about ¼-inch size. Ten grams of the ground aggregate is then placed in a ¾-inch I.D. glass tube with a stainless steel thermocouple in the middle of the mass. The glass tube is then placed in a furnace maintained at a temperature of 300° C. A gaseous mixture of hydrogen and hydrogen sulfide at a volume ratio of 10:1 ($H_2$:$H_2S$) is then passed through at a flow rate of 100 cc per minute for 5 hours. It is then cooled to room temperature over a period of 10–12 hours while continuing to pass the gaseous mixture of hydrogen and hydrogen sulfide through the catalyst. The catalyst thus obtained comprises a sulfided, interspersed mixture of cobalt oxide, aluminum oxide and zinc oxide in the following weight proportions

| Composition | Weight Percent |
|---|---|
| Cobalt oxide | 2 |
| Aluminum oxide | 73 |
| Zinc oxide | 25 |

Test of the Catalyst

The sulfided catalyst obtained above is evaluated in the synthesis of low boiling aliphatic hydrocarbons from a mixture of hydrogen and carbon monoxide is a fixed-bed reactor. In evaluating the catalyst, it is sized by screening through sieves. The catalyst particles which are used are those which pass through a U.S. Mesh No. 12 sieve and are retained on a U.S. Mesh No. 30 sieve.

The reactor consists of a 304 stainless steel tube 18 inches in length with an inside diameter of ¾-inch and an outside diameter of 3 inches. A constant temperature zone in the reactor has a volume of 25 cc. The gas inlet side of the tube is connected to a high pressure rotameter, a flow control needle valve and a pressure regulator. The outlet side of the tube is connected to a pressure condenser surrounded by ice, a flow control needle valve, a dry ice trap and flow indicators.

The synthesis gas used in the evaluation of the catalyst consists of a mixture of hydrogen and carbon monoxide in a volume ratio of 49:51 (molar ratio of hydrogen to carbon monoxide of 1:1.04).

In evaluating the catalyst of this Example 1, 8.9 gms (9.8 cc) of the sieved catalyst is placed in the tube reactor. The catalyst is maintained in place by packing each end of the reactor with ½-inch fish spine insulators. In starting the test, the synthesis gas at 1000 p.s.i.g. is passed through the system and the flow is stabilized at 18 liters per hour at room conditions. The temperature of the reactor is then increased to 400° C. over a period of about 45 minutes. The reactor is then maintained at 400° C. and a pressure of 1000 p.s.i.g. over a period of 2 hours and 10 minutes. Gas samples (2 ml) are obtained at room conditions and analyzed by a 2002 Varian Gas Chromatography Unit. At the end of the evaluation, the catalyst is cooled to room temperature and weighed. An observation is made as to whether any liquids are found in the traps. In using the catalyst of Example 1, the atomic ratio for $C_2$–$C_4$/$C_1$ in the product is 1.06. The data obtained in this test are summarized in Table 1.

EXAMPLE 2

Preparation of Catalyst

In this example, the hydroxides of cobalt and aluminum are coprecipitated and then admixed with the separately precipitated hydroxide of zinc according to the procedure which follows.

An aqueous solution of cobaltous nitrate and aluminum nitrate is prepared by dissolving 12.3 gms of cobaltous nitrate and 128.8 gms of aluminum nitrate in 2000 ml of distilled and deionized water. Ammonium hydroxide is added slowly to the aqueous solution of cobaltous nitrate and aluminum nitrate at room temperature until the pH of the solution is 6.5. The precipitate thus formed comprising a mixture of cobaltous hydroxide and aluminum hydroxide is separated from the reaction mass by filtration, washed with 500 ml of distilled water and transferred as a paste to a 1000 ml beaker (A).

An aqueous solution of zinc nitrate is prepared by dissolving 18.5 gms of zinc nitrate in 500 ml of distilled and deionized water. Ammonium hydroxide is added slowly to the aqueous solution of zinc nitrate at room temperature until the pH of the solution is 6.9. The precipitate thus formed comprising zinc hydroxide is separated from the reaction mass by filtration, washed with 500 ml of distilled water and transferred to beaker (A) containing the mixed cobaltous hydroxide and aluminum hydroxide. The volume of the three hydroxides when combined is 600 ml. After the hydroxides are thoroughly mixed, beaker (A) containing the interspersed mixture of the hydroxides is placed in an oven at 120° C. for about 24 hours. The volume of the dried precipitate which is obtained is about 50 ml.

The dried, interspersed mixture of hydroxides is then calcined and sulfided according to the procedure set forth in Example 1. The catalyst thus obtained comprises a sulfided, interspersed mixture of cobalt oxide, aluminum oxide and zinc oxide in the following weight proportions.

| Composition | Weight Percent |
|---|---|
| Cobalt oxide | 10 |
| Aluminum oxide | 70 |
| Zinc oxide | 20 |

Elemental chemical analysis of the sulfided mixture reveals a sulfur content of about 9.3 weight percent and an alkali metal content of less than 0.1 weight percent.

Test of the Catalyst

The reaction system used to evaluate the catalyst is the same as that described in Example 1. In this Example 2, however, the catalyst is reduced with hydrogen before starting the test.

The reactor is charged with 7.5 gms (8 cc) of the sieved catalyst. In starting the test, hydrogen is passed through the system at 1000 p.s.i.g. at a flow rate of 18 liters per hour at room conditions. The temperature of the reactor is then increased to 400° C. over a period of about 45 minutes. When a temperature of 400° C. is reached, the hydrogen is passed through the system for only another 10 minutes. Hydrogen is then replaced by synthesis gas comprising a mixture of hydrogen and carbon monoxide in a volume ratio of 49.51 (molar ratio of hydrogen to carbon monoxide of 1:1.04). The temperature of the reactor is maintained at 400° C. and 1000 p.s.i.g. over a period of 6 hours. Gas samples (2 ml) are obtained at room conditions and analyzed by a 2002 Varian Gas Chromatography Unit as in Example 1. In using the catalyst of Example 2, the atomic ratio for $C_2\_C_4/C_1$ in the product is 1.8. The data obtained in this test are summarized in Table 1.

of the product gas are taken at one hour and two hours, respectively. The data obtained in this test are summarized in Table 1.

Table 1

| Example No. | Catalyst* Composition weight % | | Catalyst Reduction min/° C. | CO Conversion % | S.V. hr$^{-1}$ | Final Gas : Vol.% | | | | | | Liquids Water | $\dfrac{C_2-C_4}{C_1}$ |
|---|---|---|---|---|---|---|---|---|---|---|---|---|---|
| | | | | | | $C_1$ | $C_2$ | $C_3$ | $CO_2$ | $H_2$ | CO | | |
| 1 | CoO | 2 | None | 21.3 | 1835 | 3.75 | 1.25 | 0.5 | 5.0 | 48.5 | 41.5 | t | 1.06 |
| | $Al_2O_3$ | 73 | | | | | | | | | | | |
| | ZnO | 25 | | | | | | | | | | | |
| 2 | CoO | 10 | 10/400 | 39.8 | 1636 | 5.0 | 3.0 | 1.0 | 10.0 | 44.75 | 36.25 | t | 1.8 |
| | $Al_2O_3$ | 70 | | | | | | | | | | | |
| | ZnO | 20 | | | | | | | | | | | |
| 3 | CoO | 10 | 10/425 | 49.1 | 1636 | 13.8 | 3.5 | 1.0 | 11.25 | 34.3 | 36.25 | t | 0.73 |
| | $Al_2O_3$ | 70 | | | | | | | | | | | |
| | ZnO | 20 | | | | | | | | | | | |
| 4 | CoO | 10 | 10/400 | 39.0 | 2250 | 6.3 | 1.5 | 0.5 | 5.0 | 61.5 | 25.0 | t | 0.69 |
| | $Al_2O_3$ | 70 | | | 30.9 | 2250 | 6.5 | 2.5 | 0.3 | 7.5 | 45.7 | 37.5 | t | 0.91 |
| | ZnO | 20 | | | | | | | | | | | |

*Interspersed mixture of oxides of cobalt, aluminum and zinc for subsequent sulfiding. Cobalt oxide is presented as cobaltous oxide (CoO) for convenience in providing weight percent values.
t = trace, <1 ml for 4 cu. ft. of feed gas
$\dfrac{C_2-C_4}{C_1}$ = atomic ratio for carbon in $C_1$, $C_2$, $C_3$, $C_4$ hydrocarbons

EXAMPLE 3

Preparation of Catalyst and Test of the Catalyst

The catalyst in this example is the same as that in Example 2. In this example, however, the synthesis reaction is conducted at 425° C. instead of 400° C. as in Example 2. The atomic ratio for $C_2\_C_4/C_1$ in the product is 0.73. The data obtained in this test are summarized in Table 1.

EXAMPLE 4

Preparation of the Catalyst

In this example the hydroxides of cobalt, aluminum and zinc are separately precipitated according to Example 1. The amounts of the materials used and the conditions of operation are the same as those used in Example 2. The cobaltous nitrate and the aluminum nitrate are dissolved separately in 500 ml and 1500 ml, respectively, of distilled water. The separate hydroxide filter cakes are mixed together and dried at 120° C. for 16 hours. The dried, interspersed mixture of hydroxides is reduced by flowing hydrogen thereover for two hours at 350° C., and then sulfided by flowing a gaseous mixture of hydrogen and hydrogen sulfide at a volume ratio of 10:1 ($H_2:H_2S$) at a flow rate of 100 cc./min. at 350° C. for 20 hours. The catalyst thus obtained comprises a sulfided, interspersed mixture of cobalt oxide, aluminum oxide and zinc oxide in the following weight proportions.

| Composition | Weight Percent |
|---|---|
| Cobalt oxide | 10 |
| Aluminum oxide | 70 |
| Zinc oxide | 20 |

Elemental chemical analysis of the sulfided mixture reveals a sulfur content of about 8.1 weight percent and an alkali metal content of less than 0.1 weight percent.

Test of the Catalyst

The catalyst is reduced with hydrogen and further evaluated as in Example 2. The atomic ratio for $C_2\_C_4/C_1$ in the product is 0.69 and 0.91 when samples of the product gas are taken at one hour and two hours, respectively. The data obtained in this test are summarized in Table 1.

It will be noted from the data summarized in Table 1 that good yields of low boiling aliphatic hydrocarbons are obtained with a catalyst of the invention. It will be further noted, however, that the best $C_2\_C_4/C_1$ ratio is obtaind when the cobalt and aluminum hydroxides are coprecipitated and when the temperature of the synthesis reaction is maintaind at 400° C. as in Example 2.

While my invention has been described above with reference to various specific examples and embodiments, it will be understood that the invention is not limited to such examples and embodiments and may be variously practiced within the scope of the claims hereinafter made.

I claim:

1. A catalyst for use in the synthesis of low boiling aliphatic hydrocarbons from hydrogen and carbon monoxide which comprises a sulfided, interspersed mixture of cobalt oxide aluminum oxide and zinc oxide, which mixture by elemental analysis contains less than about 0.5 weight percent of alkali metal, said catalyst prior to sulfiding comprising about 1 to about 15 weight percent of cobalt oxide, about 55 to about 85 weight percent of aluminum oxide and about 15 to about 30 weight percent of zinc oxide, the sulfur content by elemental analysis of the catalyst comprising about 2.0 to about 12.0 percent by weight of the final catalyst composition.

2. A catalyst composition according to claim 1 wherein the cobalt oxide comprises about 2 to about 10 weight percent of the catalyst, the aluminum oxide comprises about 70 to about 80 weight percent of the catalyst and the zinc oxide comprises about 20 to about 25 weight percent of the catalyst.

3. A catalyst composition according to claim 1 wherein the cobalt oxide comprises about 10 weight percent of the catalyst, the aluminum oxide comprises about 70 weight percent of the catalyst and the zinc oxide comprises about 20 weight percent of the catalyst.

4. A catalyst according to claim 2 wherein the interspersed mixture was sulfided by hydrogen sulfide to said sulfur content.

* * * * *